United States Patent [19]

Babcock et al.

[11] 4,004,003
[45] Jan. 18, 1977

[54] 25-HYDROXYCALCIFEROL COMPOUNDS FOR TREATMENT OF STEROID-INDUCED OSTEOPOROSIS

[75] Inventors: John C. Babcock; J. Allan Campbell, both of Kalamazoo, Mich.

[73] Assignee: The Upjohn Company, Kalamazoo, Mich.

[22] Filed: Oct. 6, 1975

[21] Appl. No.: 619,647

Related U.S. Application Data

[63] Continuation of Ser. No. 501,039, Aug. 28, 1974, abandoned, which is a continuation-in-part of Ser. No. 807,929, March 17, 1969, Pat. No. 3,833,622.

[52] U.S. Cl. ............................ 424/238; 260/397.2
[51] Int. Cl.² ......................................... C07J 9/00
[58] Field of Search ................. 260/397.2; 424/238

[56] References Cited

UNITED STATES PATENTS 3,772,361  11/1973  De Luca et al. ............... 260/397.2
3,901,928  8/1975   Hesse et al. .................... 260/397.2

*Primary Examiner*—Elbert L. Roberts
*Attorney, Agent, or Firm*—John J. Killinger; Roman Saliwanchik

[57] ABSTRACT

A process for the prevention or treatment of osteoporosis induced as a side effect of the administration of glucocorticoid steroids by the administration of a compound of the formula:

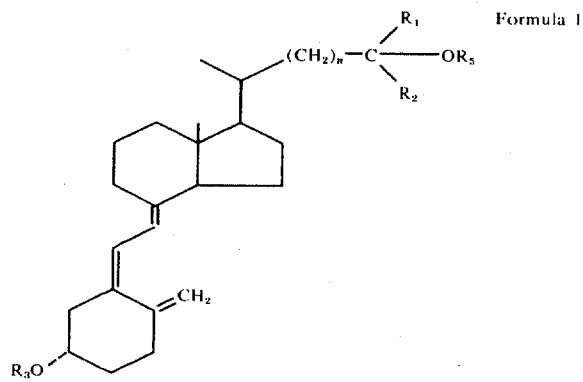

wherein $R_1$ and $R_2$ are the same or different radicals selected from the group consisting of hydrogen, alkyl of less than 9 carbon atoms, and phenyl; $R_3$ and $R_5$ are selected from the group consisting of hydrogen and lower acyl; $n$ is an integer, selected from the group consisting of 2, 3, and 4; or a hydrate thereof in association with a pharmaceutical carrier to a human or animal being treated or having been treated with a glucocorticoid hormone.

3 Claims, No Drawings

25-HYDROXYCALCIFEROL COMPOUNDS FOR TREATMENT OF STEROID-INDUCED OSTEOPOROSIS

CROSS REFERENCE TO RELATED APPLICATIONS

This is a continuation of application Ser. No. 501,039 filed Aug. 28, 1974, now abandoned, which is a continuation-in-part of application Ser. No. 807,929, filed Mar. 17, 1969, now U.S. Pat. No. 3,833,622.

BRIEF SUMMARY OF THE INVENTION

This invention relates to therapy for prophylactic or therapeutic treatment of osteoporosis which results from the administration of gluco-corticoid hormones, either natural or synthetic.

DETAILED DESCRIPTION OF THE INVENTION

Osteoporosis, a softening of the bone due to calcium loss, has been recognized as an undesirable side effect due to the administration of gluco-corticoid hormones [Curtiss, P. H., Clark, W. S., and C. H. Herndon, J. Amer. Med. Assoc., 156:467 (1954); Bradley, B. W., and B. M. Anssell, Ann. Rheum. Dis. 19:135 (1960); and Saville, P. D., and O. Kharmosh, Arth. Rheum. 10:423 (1967)].

In accordance with the present invention, it has been found that this drug-induced osteoporosis can be prevented or treated by administering a compound of the Formula I either concurrently with the administration of the gluco-corticoid compounds or subsequent to termination of gluco-corticoid therapy.

The compounds useful in the process of the present invention are illustrated by the Formula:

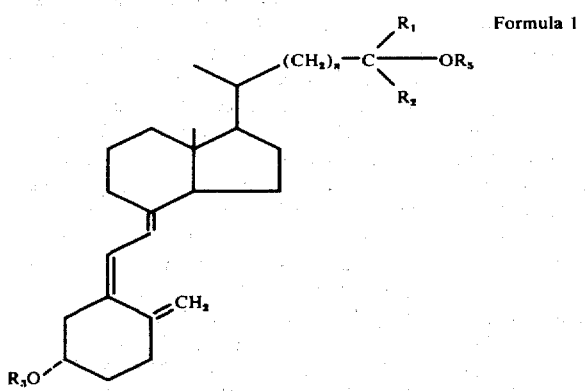

Formula 1 wherein $R_1$ and $R_2$ are the same or different radicals selected from the group consisting of hydrogen, alkyl of less than 9 carbon atoms, and phenyl; $R_3$ and $R_5$ are selected from the group consisting of hydrogen and lower acyl; $n$ is an integer, selected from the group consisting of 2, 3, and 4; or a hydrate thereof.

The acyl radicals can be those of hydrocarbon carboxylic acids of less than 12 carbon atoms as exemplified by the lower alkanoic acids (e.g., acetic, propionic, butyric, and tert-pentanoic acid), the lower alkanoic acids, the monocyclic aryl carboxylic acids (e.g., benzoic and toluic acid), the monocyclic aryl lower alkanoic acids (e.g., phenacetic and β-phenylpropionic acid), the cycloalkane carboxylic acids and the cycloalkene carboxylic acids. The alkyl radicals are those of hydrocarbon alkyl radicals of less than 9 carbon atoms as exemplified by the lower alkyl radicals (e.g., methyl, ethyl, propyl, isopropyl, butyl, octyl) and the lower cycloalkyl radicals (e.g., cyclopropyl, cyclopentyl, cyclohexyl).

The foregoing compounds can be prepared by methods disclosed in co-pending application Ser. No. 807,929, filed Mar. 17, 1969, now allowed.

The compositions of the present invention are presented for administration to humans and animals in unit dosage forms, such as tablets, capsules, pills, powders, granules, sterile parenteral solutions or suspensions, and oral solutions or suspensions, and oil-in-water and water-in-oil emulsions containing suitable quantities of the compound of Formula I.

For oral administration either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, aerosols with metered discharges, segregated multiples of any of the foregoing, and other forms as herein described.

The dosage of a compound of the Formula I for the prophylactic or therapeutic treatment of steroid-induced osteoporosis is from about 50 to about 25,000 I.U./day or from about 1 to about 500 micrograms/day. The higher doses ordinarily being used for therapeutic treatment of established osteoporosis and the lower dosages being used as a prophylactic measure.

EXAMPLE 1

A lot of 10,000 tablets, each containing 500 micrograms of 25-hydroxycholcalciferol is prepared from the following types and amounts of ingredients:

| | |
|---|---|
| 25-hydroxycholecalciferol hydrate | 5 gm. |
| Dicalcium phosphate | 1,500 gm. |
| Methcellulose, U.S.P. (15 cps.) | 60 gm. |
| Talc | 150 gm. |
| Corn Starch | 200 gm. |
| Calcium stearate | 12 gm. |

The compound and dicalcium phosphate are mixed well, granulated with 7.5 percent solution of methcellulose in water, passed through a No. 8 screen and dried carefully. The dried granules are passed through a No. 12 screen, mixed thoroughly with the talc, starch and magnesium stearate, and compressed into tablets.

The tablets are useful in treating steroid-induced osteoporosis at a dose of 1 tablet daily for an adult human.

EXAMPLE 2

One thousand two-piece hard gelatin capsules, each containing 50 micrograms of 25-hydroxycholecalciferol are prepared from the following types and amounts of ingredients:

| | |
|---|---|
| 25-hydroxycholecalciferol hydrate | 50 mg. |
| Talc | 100 gm. |
| Magnesium stearate | 10 gm. |

The ingredients are mixed well and filled into capsules of the proper size.

Capsules so prepared are useful in treating steroid-induced osteoporosis at a dose of one capsule 3 times a day.

EXAMPLE 3

One thousand tablets, each containing 1 microgram of 25-hydroxycholecalciferol are made from the following types and amounts of ingredients:

| | |
|---|---|
| 25-hydroxycholecalciferol hydrate | 1 mg. |
| Microcrystalline cellulose NF | 120 gm. |
| Starch | 16 gm. |
| Magnesium stearate powder | 4 gm. |

The ingredients are screened and blended together and pressed into 1 gm. tablets.

The tablets are useful to protect against steroid-induced osteoporosis at a dose of 1 tablet daily during the administration of hydrocortisone therapy for asthma.

EXAMPLE 4

A sterile preparation suitable for intramuscular injection and containing 500 micrograms of 25-hydroxycholecalciferol in each milliliter is prepared from the following ingredients:

| | |
|---|---|
| 25-hydroxycholecalciferol | 0.5 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected I.M. daily for the treatment of steroid-induced osteoporosis.

EXAMPLE 5

Following the procedure of the preceding Examples 1 through 4, inclusive, substituting an equimolar amount of each of 25-hydroxycholecalciferol 3-propionate, 25-hydroxycholecalciferol 3-isobutyrate, 25-hydroxycholecalciferol 3-hexanoate, 25-hydroxycholecalciferol 3-cyclopentylpropionate, 25-hydroxycholecalciferol 3-decanoate, 25-hydroxycholecalciferol 3-cyclohexanecarboxylate, 25-hydroxycholecalciferol 3-benzoate, 26,27-bisnor-25,25-dioctyl-3$\beta$-hydroxycholesta-5-cis-7,10(19)-triene-3$\beta$,25-diol, 26,27-bisnor-25,25-dibutyl-3$\beta$-hydroxycholesta-5-cis-7,10(19)-triene-3$\beta$,25-diol, 26,27-bisnor-25,25-diisopropyl-3$\beta$-hydroxycholesta-5-cis-7,10(19)-triene-3$\beta$,25-diol, 26,27-bisnor-25,25-dicyclopentyl-3$\beta$-hydroxycholesta-5-cis-7,10(19)-triene-3$\beta$,25-diol, 26,27-bisnor-25,25-diphenyl-3$\beta$-hydroxycholesta-5-cis-7,10(19)-triene-3$\beta$,25-diol, 9,10-secocholesta-5-cis-7,10(19)-triene-3$\beta$,25-diol dipropionate, 9,10-secocholesta-5-cis-7,10(19)-triene-3$\beta$,25-diol diisobutyrate, 9,10-secocholesta-5-cis-7,10(19)-triene-3$\beta$,25-diol dihexanoate, 9,10-secocholesta-5-cis-7,10(19)-triene-3$\beta$,25-diol dibenzoate, 9,10-secocholesta-5-cis-7,10(19)-triene-3$\beta$,25-diol dicyclohexylacetate, 9,10-seco-24-homocholesta-4-cis-7,10(19)triene-3$\beta$,25-diol diacetate, 9,10-seco-24-norcholesta-5-cis-7,10(19)-triene-3$\beta$,25-diol diacetate, 9,10-secocholesta-5-cis-7,10(19)-triene-3$\beta$,25-diol 25-propionate, 9,10-secocholesta-5-cis-7,10(19)-triene-3$\beta$,25-diol 25-isobutyrate, 9,10-secocholesta-5-cis-7,10(19)-triene-3$\beta$,25-diol 25-hexanoate, 9,10-secocholesta-5-cis-7,10(19)-triene-3$\beta$,25-diol 25-benzoate, 9,10-secocholesta-5- cis-7,10(19)-triene-3β,25-diol 25-cyclohexylacetate, 9,10-seco-24-homocholesta-5-cis-7,10(19)-triene-3β,25-diol 25-acetate, 9,10-seco-24-norcholesta-5-cis-7,10(19)-triene-3β,25-diol 25-acetate, 9,10-secocholesta-5-cis-7,10(19)-triene-3β,25-diol 3-propionate, 9,10-secocholesta-5-cis-7,10(19)-triene-3β,25-diol 3-isobutyrate, 9,10-secocholesta-5-cis-7,10(19)-triene-3β,25-diol 3-hexanoate, 9,10-secocholesta-5-cis-7,10(19)-triene-3β,25-diol 3-benzoate, 9,10-secocholesta-5-cis-7,10(19)-triene-3β,25-diol 3-cyclohexylacetate, 9,10-seco-24-homocholesta-5-cis-7,10(19)-triene-3β,25-diol 3-acetate, and 9,10-seco-24-norcholesta-5-cis-7,10(19)-triene-3β,25diol 3-acetate.

We claim:

1. A process for the therapeutic or prophylactic treatment of gluco-corticoid hormone-induced osteoporosis comprising the administration of a compound of the formula:

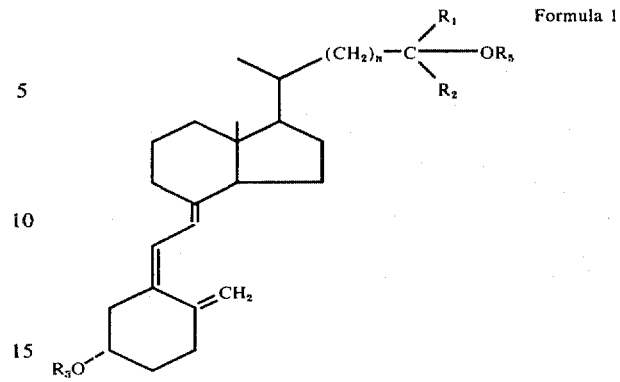

Formula 1 wherein $R_1$ and $R_2$ are the same or different radicals selected from the group consisting of hydrogen, alkyl of less than 9 carbon atoms, and phenyl; $R_3$ and $R_5$ are selected from the group consisting of hydrogen and lower acyl; $n$ is an integer, selected from the group consisting of 2, 3, and 4; or a hydrate thereof in association with a pharmaceutical carrier to a human or animal.

2. The process of claim 1 wherein the amount of compound administered is from about 1 to about 500 micrograms per day.

3. The process of claim 1 wherein the compound administered is 25-hydroxycholecalciferol.

* * * * *